United States Patent [19]

Stühler

[11] Patent Number: 4,562,007

[45] Date of Patent: Dec. 31, 1985

[54] PROCESS FOR PREPARING CARBOXYLIC ACID ESTERS OF HEXITOLS

[75] Inventor: Herbert Stühler, Burgkirchen, Fed. Rep. of Germany

[73] Assignee: Hoechst Aktiengesellschaft, Fed. Rep. of Germany

[21] Appl. No.: 548,286

[22] Filed: Nov. 3, 1983

[30] Foreign Application Priority Data

Nov. 5, 1982 [DE] Fed. Rep. of Germany ....... 3240892

[51] Int. Cl.$^4$ ............................ C09F 5/08; C09F 7/10; C11C 3/00
[52] U.S. Cl. ................................................. 260/410.6
[58] Field of Search ........................ 260/410.6, 410.7

[56] References Cited

U.S. PATENT DOCUMENTS

| | | | |
|---|---|---|---|
| 2,322,820 | 6/1943 | Brown | 260/410.6 X |
| 2,322,821 | 6/1943 | Brown | 260/410.6 X |
| 2,996,387 | 8/1961 | Radlove | 260/410.6 |
| 2,997,492 | 8/1961 | Martin | 260/410.6 |
| 3,579,547 | 5/1971 | Traxler | 260/410.6 |
| 3,637,774 | 1/1972 | Babayan et al. | 260/404 X |
| 4,065,418 | 12/1977 | Foulks, Jr. et al. | 260/410.9 R X |
| 4,297,290 | 10/1981 | Stockburger | 260/410.6 |
| 4,363,763 | 12/1982 | Peterson | 260/410.7 |

*Primary Examiner*—Helen M. S. Sneed
*Attorney, Agent, or Firm*—Connolly and Hutz

[57] ABSTRACT

A process is described for preparing carboxylic acid esters of hexitols by rapidly heating the hexitol and carboxylic acid to 210° to 250° C. in the presence of alkaline catalysts, continuing the esterification reaction at this temperature, while simultaneously driving off the water formed, until an acid number of 2 to 15 has been reached, and then rapidly cooling down to at least 145° C. This process produces hexitol carboxylates which are essentially free of anhydro compounds and have good color quality. The hexitol carboxylates are surface-active substances, in particular high-grade emulsifiers and lubricants.

4 Claims, No Drawings

PROCESS FOR PREPARING CARBOXYLIC ACID ESTERS OF HEXITOLS

The invention relates to a process for preparing carboxylic acid esters of hexitols by reacting hexitols with carboxylic acids in the presence of alkaline catalysts and an inert gas atmosphere while stirring and while removing the water formed in the course of the esterification, to produce esters which are essentially free of anhydro compounds and possess a good color quality.

In the preparation of carboxylic acid esters of hexitols the critical point is to avoid the formation of the less hydrophilic anhydrohexitols and anhydrohexitol carboxylates. These undesirable anhydro compounds, for example monoanhydrosorbitol (sorbitan), dianhydrosorbitol (isosorbitol) and the corresponding carboxylic acid esters, are known to form by dehydration reactions in which one or more moles of water are eliminated intramolecularly. Another aim is to obtain good color quality.

Because of the great importance of the carboxylic acid esters of hexitols, numerous attempts have already been made to find a process for preparing these esters which produces as little anhydro compound as possible and affords good color quality.

A number of patent specifications, for example U.S. Pat. Nos. 2,997,492 and 2,997,493, recommend preparing the carboxylic acid esters of hexitols by means of transesterification processes. These produce relatively undiscolored esters which are moreover essentially free of anhydro groups. However, these known transesterification processes necessitate the use of certain carboxylic acid esters and specific solvents.

Numerous other patent specifications, for example U.S. Pat. Nos. 1,959,930 and 3,579,547, attempt to prevent the formation of anhydro groups and of highly colored byproducts by using fatty acid chlorides, fatty acid anhydrides and the like for esterifying the hexitols, or by not starting from hexitols directly, but from hexitol derivatives, i.e. from hexitols bearing protective groups.

Finally, processes have also already been described to start advantageously directly from carboxylic acid and hexitol. However, even all these processes for preparing carboxylic acid esters of hexitols with good color quality and a relatively low anhydro compound content, disclosed, for example, by British Pat. No. 872,507 and German Offenlegungsschrift 2,423,278, still leave something to be desired, because they require special solvents, long reactions, relatively high catalyst levels and the like.

In the process described in British Pat. No. 872,507, the reaction of carboxylic acid and hexitol, which is carried out at a temperature of about 97° C., necessitates the use of a special solvent, namely dimethylformamide.

In the process described in German Offenlegungsschrift No. 2,423,278, hexitol is reacted (esterified) at a temperature of 100° C. to 190° C. with carboxylic acid (fatty acid) in the presence of at least 10% by weight of fatty acid soap as a catalyst and in an inert gas atmosphere while stirring and while removing the water formed in the course of the esterification. The process has the disadvantage that the reaction takes a relatively long time, and the necessary amount of catalyst is relatively high.

It is therefore an object of the invention to provide a process for preparing carboxylic acid esters of hexitols which will make it possible to start directly from carboxylic acid and hexitol without a special solvent, which will yield the carboxylic acid esters in good color quality and only slightly contaminated with anhydro compounds, and which will furthermore have yet further advantages, in particular the advantage of a short reaction time.

The novel process for preparing carboxylic acid esters of hexitols by reacting hexitols with carboxylic acids in the presence of alkaline catalysts and an inert gas atmosphere while stirring and while removing the water formed in the course of the esterification comprises (a) using hexitol and carboxylic acid in a molar ratio of 1:0.3 to 1:2.3, (b) using the alkaline catalyst in an amount of 0.01 to 1% by weight, relative to the amount of hexitol, (c) heating up rapidly to a temperature of 210° C. to 250° C. and reacting at that temperature, (d) continuing the reaction until an acid number of 2 to 15 has been reached, and (e) cooling down rapidly to at least 145° C. when this acid number has been reached.

The carboxylic acids which are used in the process according to the invention are the aliphatic, straight-chain or branched, preferably straight-chain; and saturated or unsaturated (preferably monounsaturated to triply unsaturated) monocarboxylic acids.

Preferred carboxylic acids are fatty acids, advantageously those of 6 to 30 carbon atoms, preferably of 8 to 22 carbon atoms. It is also possible to use mixtures of carboxylic acids, preferably fatty acid mixtures. Examples of advantageous carboxylic acids are hexanoic acid (caproic acid), octanoic acid (caprylic acid), decanoic acid (capric acid), dodecanoic acid (lauric acid), tetradecanoic acid (myristic acid), hexadecanoic acid (palmitic acid), octadecanoic acid (stearic acid), eicosanoic acid (arachidic acid), docosanoic acid (behenic acid), dodecenoic acid (lauroleic acid), tetradecenoic acid (myristoleic acid), hexadecenoic acid (palmitoleic acid), octadecenoic acid (oleic acid), 12-hydroxyoctadecenoic acid (ricinoleic acid), octadecadienoic acid (linoleic acid) and octadecatrienoic acid (linolenic acid) as well as coconut oil acid, tallow fat acid and palm kernel fat acid. Fat coconut acid generally has the following typical chain distribution in percent by weight: saturated: $C_6$ 0.5%, $C_8$ 8%, $C_{10}$ 7%, $C_{12}$ 48%, $C_{14}$ 17%, $C_{16}$ 9% and $C_{18}$ 2%; unsaturated: $C_{16}$ (with one double bond) 0.2%, $C_{18}$ (with one double bond) 7% and $C_{18}$ (with 2 double bonds) 1.3%. Tallow fat acid generally has the following typical chain distribution: saturated $C_{12}$ 0.5%, $C_{14}$ 3%, $C_{15}$ 1%, $C_{16}$ 25%, $C_{17}$ 2%, $C_{18}$ 19% and $C_{20}$ 1%; unsaturated: $C_{14}$ (with one double bond) 0.5%, $C_{16}$ (with one double bond) 3%, $C_{18}$ (with one double bond) 40%, $C_{18}$ (with two double bonds) 4% and $C_{18}$ (with three double bonds) 1%.

Palm kernel fat acid generally has the following typical chain distribution in percent by weight: saturated: $C_6$ 0.5%, $C_8$ 4%, $C_{10}$ 5%, $C_{12}$ 50%, $C_{14}$ 15%, $C_{16}$ 7% and $C_{18}$ 2%; unsaturated: $C_{16}$ (with one double bond) 0.5%, $C_{18}$ (with one double bond) 15% and $C_{18}$ (with two double bonds) 1%. The carboxylic acids are generally used as such, i.e. in the absence of any solvent whatsoever.

The hexitols which are used in process according to the invention are the hexahydric saturated and straight-chain aliphatic alcohols of 6 carbon atoms, such as sorbitol, mannitol, dulcitol, iditol, talitol and alitol, and their ethoxylates and propoxylates having 1 to 10, preferably 1 to 5, ethylene oxide units, or, respectively, 1 to 5, preferably 1 to 3, propylene oxide units, per mole of hexitol. Preferred hexitols are sorbitol, mannitol and dulcitol and their ethoxylates and propoxylates having 1 to 5 ethylene oxide units and, respectively, 1 to 3 propylene oxide units per mole of hexitol.

Like the carboxylic acids, the hexitols are also generally used in that form in which they generally exist. Mannitol and dulcitol, for example, can be obtained in the form of solids and are therefore used as such. Sorbitol can be obtained either as a solid or as an aqueous solution (sirup). It can be used in either form. If an aqueous solution is used, the water in the solution will already be evaporated off in the course of heating to the specified reaction temperature.

According to the invention, the molar ratio of hexitol to carboxylic acid is 1:0.3 to 1:2.3, preferably 1:0.5 to 1:2.

Alkaline catalysts are used in the reaction according to the invention. The amount of catalyst is 0.01 to 1% by weight, preferably 0.1 to 0.5% by weight, relative to the weight of hexitol.

Examples of suitable alkaline (basic) catalysts are alkali metal hydroxides, alkali metal carbonates, alkali metal alcoholates having an alkyl group of 1 to 4 carbon atoms, and/or alkali metal oxides. Preferred catalysts are, singly or mixed, alkali metal hydroxides, such as potassium hydroxide and sodium hydroxide, alkali metal carbonates, such as potassium carbonate and sodium carbonate, and alkali metal alcoholates having an alkyl group of 1 to 2 carbon atoms, such as potassium methylate and sodium methylate.

In the process according to the invention, the esterification of hexitol with carboxylic acid is carried out at a temperature of 210° C. to 250° C., preferably 220° C. to 240° C., and the heating-up to the reaction temperature according to the invention should be rapid, preferably within a period of at most 45 minutes. The heating-up period generally is, depending on the size of the batch, 20 to 40 minutes. If water is present as a solvent, for example if the abovementioned aqueous sorbitol solution is used, the water in the solution is distilled off in the heating-up phase at initially about 100° C. It is clear that the time for distilling off this water has not been included in the specified heating-up period. If water is present as a solvent, the specified heating-up period thus essentially relates to the time which should be required at most to heat from about 100° C. (after the water in the solution has been distilled off) to the reaction temperature according to the invention.

The rapid heating to the reaction temperature can be achieved using the aids known for this type of purpose, for example using a Pilz-type heating mantle, a hot oil cycle or the like.

The mixture of hexitol, carboxylic acid and catalyst is held at the reaction temperature according to the invention until the acid number of the mixture is 2 to 15, preferably 4 to 10. This generally takes a reaction time of 10 to 60 minutes. When the acid number has been reached, the mixture is cooled down rapidly, namely preferably in at most 40 minutes, to at least 145° C. The temperature to which the reaction product is rapidly cooled is preferably 120° to 20° C. The time it takes to cool down the reaction product depends on the size of the batch, the level of the reaction temperature and the cooling method and is in general 5 to 30 minutes. The rapid cooling can be achieved using aids known for this purpose, for example using a cooling bath, a coolant cycle or the like.

The reaction according to the invention is carried out while stirring in an inert gas atmosphere. The inert gases can be gases which do not react with the starting materials or the reaction product. Nitrogen, carbon dioxide and/or noble gases are preferred. The inert gas atmosphere in the process according to the invention is preferably produced by passing an inert gas stream over or through the reaction mixture. The stream is generally, per kilogram of reaction mixture, 5 to 30 liters pre hour, preferably 10 to 20 liters per hour.

The reaction according to the invention is generally carried out under atmospheric pressure (standard pressure). It can also be carried out under reduced pressure. The vacuum can vary within wide limits. Its limit is merely where reaction components or reaction products might also be driven off. If reduced pressure is used, the pressure is advantageously 100 to 5,000 Pa, preferably 2,000 to 4,000 Pa.

The reaction can be carried out continuously, for example in a coil, or discontinously, for example batchwise in a reaction vessel.

The water formed in the course of the esterification is continuously removed. The removal of water from the reaction system already takes place as a result of the high reaction temperature. The inert gas stream and, as the case may be, prevailing reduced pressure likewise drive out any water present.

The reaction product of the process according to the invention, which is in existence when the specified acid number has been reached and after the cooling down, is a more or less viscous liquid or a solid and generally consists of a mixture of individual hexitol carboxylates. Depending on the reaction conditions and the molar ratio of hexitol to carboxylic acid, it contains in the main hexitol monocarboxylate and hexitol dicarboxylate.

Since the reaction product can already be used as such for many purposes, it is generally not necessary to isolate individual esters or groups of esters. However, it can be advantageous to remove catalysts present in the product and any unconverted hexitol and unconverted carboxylic acid, for example by washing with aqueous solutions of salts, such as sodium chloride and sodium sulfate.

The process according to the invention produces hexitol carboxylates which are essentially free of anhydro compounds and which are only relatively slightly colored. Their degree of coloring is generally no more than that of the intrinsic color of the carboxylic acid used.

If carboxylic acid esters having a particularly good color quality are desired, the reaction product can be subjected to a relevant treatment, preferably to a bleach. In a preferred embodiment, the bleach is preformed by adding to the reaction product, at a temperature of 50° C. to 120° C., preferably 70° C. to 100° C., about 0.5 to 5% by weight, preferably about 1 to 3% by weight, relative to the weight of the reaction product, of an approximately 35% by weight strength aqueous hydrogen peroxide solution and stirring at said temperature for about 10 to 30 minutes (the reaction product does not became any lighter), whereupon the water introduced by the hydrogen peroxide treatment is distilled off, and the residue (the reaction product) is advantageously additionally filtered with or without suction. The water is preferably distilled off at a temperature of 60° C. to 120° C. under a vacuum of 500 to 2,000 Pa.

The hexitol carboxylates prepared by the process according to the invention are useful surface-active substances, in particular emulsifiers and lubricants. They are advantageously used, for example, for preparing water-in-oil or oil-in-water emulsions, in the formulation of cosmetic products, in the detergent industry and as lubricants in plastics processing. With these or other types of use, it can be advantageous, in certain circumstances, to vary the surface-active properties of the carboxylic acid esters prepared according to the invention, for example by ethoxylation and/or propoxylation.

The invention will now be explained in more detail by means of examples.

EXAMPLES 1 TO 10

A 2-liter reaction vessel which had been equipped with a thermometer, a stirrer, a water separator and a device for passing through an inert gas was separately charged with carboxylic acid, hexitol and alkaline catalyst. The reaction mixture was rapidly heated, and melted where appropriate, with stirring and passing through of about 20 liters of nitrogen per hour and per kg of reaction mixture by means of a Pilz-type heating mantle to the temperature according to the invention, and was held at this temperature while stirring. The water formed (under atmospheric pressure) in the course of the conversion (from the esterification reaction) was simultaneously taken off via the water-separator. When the target acid number according to the invention had been reached, the reaction product was cooled by means of cooling air and/or a cooling water bath so that it rapidly took on a temperature (cooling-down temperature) which was below the temperature limit according to the invention.

The hydroxyl number (OH number) was determined in each case to characterize the product obtained. The acid number and the OH number were determined by the "Einheitsmethoden der deutschen Gesellschaft für Fettwissenschaft" ("Standard Methods of the German Society for Fat Science").

The following table shows how Examples 1 to 10 were performed in detail. The table also contains the measured OH numbers and the calculated (theoretical) OH numbers.

TABLE

| Examples | mole of hexitol | mole of fatty acid | Catalyst and amount (%) | Temperature (°C.) | Heating period (min) | Acid number | Reaction time (min) | Cooling time (min) | Cooling-down temperature (°C.) | Measured OH number | Calculated OH number |
|---|---|---|---|---|---|---|---|---|---|---|---|
| 1 | 2.5 sorbitol | 2.5 coconut fat acid | NaOH 0.4 | 240 | 35 | 4 | 15 | 20 | 140 | 678 | 768 |
| 2 | 1.5 sorbitol | 3 coconut fat acid | NaOH 0.4 | 240 | 30 | 10 | 10 | 25 | 110 | 346 | 409 |
| 3 | 1.5 mannitol | 3 oleic acid | NaOH 0.4 | 240 | 40 | 13 | 10 | 5 | 145 | 258 | 316 |
| 4 | 2 dulcitol | 2 iso-stearic acid | NaOH 0.4 | 240 | 35 | 5 | 40 | 10 | 100 | 419 | 594 |
| 5 | 3 sorbitol | 1.5 stearic acid | NaOH 0.4 | 220 | 30 | 15 | 55 | 10 | 80 | 840 | 967 |
| 6 | 2.5 sorbitol + 2 EO | 0.75 coconut fat acid | KOH 0.5 | 210 | 25 | 2 | 20 | 35 | 60 | 585 | 594 |
| 7 | 2 mannitol + 4 EO | 1 coconut fat acid | $Na_2CO_3$ 0.1 | 220 | 35 | 2 | 20 | 40 | 145 | 515 | 500 |
| 8 | 2 sorbitol + 1 PyO | 2 coconut fat acid | $NaOCH_3$ 0.08 | 250 | 45 | 3 | 10 | 5 | 130 | 558 | 665 |
| 9 | 1 sorbitol + 3 PyO | 2.3 coconut fat acid | NaOH 0.2 | 240 | 40 | 6 | 45 | 15 | 65 | 260 | 268 |
| 10 | 2 dulcitol + 1 EO | 2 stearic acid | NaOH 0.2 | 240 | 40 | 3 | 25 | 40 | 30 | 524 | 565 |

EO = ethylene oxide
PyO = propylene oxide

I claim:

1. A process for preparing carboxylic acid esters of hexitols by reacting hexitols with carboxylic acids in the presence of alkaline catalysts and an inert gas atmosphere while stirring and while removing the water formed in the course of the esterification, which comprises
    (a) using hexitol and carboxylic acid in a molar ratio of 1:0.5 to 1:2,
    (b) using the alkaline catalyst in an amount of 0.1 to 0.5% by weight, relative to the amount of hexitol,
    (c) heating up rapidly to a temperature of 220° to 240° C. and reacting at that temperature,
    (d) continuing the reaction until an acid number of 4 to 10 has been reached, and
    (e) cooling down rapidly to a temperature of 120° to 20° C. when this acid number has been reached.

2. The process as claimed in claim 1, wherein the reaction mixture is heated to the reaction temperature within a period of at most 45 minutes, and the reaction product is cooled down after the acid number has been reached within a period of at most 40 minutes.

3. The process as claimed in claim 2, wherein the heating up takes 20 to 40 minutes and the cooling down takes 5 to 30 minutes.

4. The process as claimed in claim 1, wherein the hexitol used is sorbitol, mannitol, dulcitol or their ethoxylates or propoxylates having 1 to 5 ethylene oxide units or, respectively, 1 to 3 propylene oxide units per mole of hexitol, and the carboxylic acid used is a fatty acid.

* * * * *